(12) United States Patent
Tilton, Jr. et al.

(10) Patent No.: US 6,416,506 B1
(45) Date of Patent: *Jul. 9, 2002

(54) INSTRUMENTATION FOR ENDOSCOPIC SURGICAL INSERTION AND APPLICATION OF LIQUID, GEL AND LIKE MATERIAL

(76) Inventors: Eugene B. Tilton, Jr., 513 Dorrington Blvd., Metairie, LA (US) 70005; David Wiseman, 6757 Arapaho, Suite 711, Dallas, TX (US) 75248

( * ) Notice: Subject to any disclaimer, the term of this patent is extended or adjusted under 35 U.S.C. 154(b) by 0 days.

This patent is subject to a terminal disclaimer.

(21) Appl. No.: 09/376,803

(22) Filed: Aug. 18, 1999

Related U.S. Application Data (63) Continuation-in-part of application No. 09/021,564, filed on Feb. 10, 1998, now Pat. No. 6,010,495, which is a continuation-in-part of application No. 08/718,861, filed on Sep. 24, 1996, now Pat. No. 5,797,899, which is a continuation-in-part of application No. 08/644,504, filed on May 10, 1996, now Pat. No. 5,766,157, which is a continuation-in-part of application No. 08/625,098, filed on Apr. 1, 1996, now Pat. No. 5,919,184, which is a continuation-in-part of application No. 08/407,409, filed on Mar. 17, 1995, now Pat. No. 5,503,623.

(51) Int. Cl.⁷ ............................................... A61B 17/00
(52) U.S. Cl. ............................................................ 606/1
(58) Field of Search ...................... 606/1, 51; 604/181, 604/28, 13, 15; 600/563, 573

(56) References Cited

U.S. PATENT DOCUMENTS

| | | | |
|---|---|---|---|
| 3,154,079 A | 10/1964 | McKay | 604/264 |
| 3,892,226 A | 7/1975 | Rosen | 604/264 |
| 4,722,725 A | 2/1988 | Sawyer et al. | 604/44 |
| 4,729,764 A | 3/1988 | Gaultier | 128/750 |
| 4,842,580 A | 6/1989 | Oulette | 128/750 |
| 4,904,238 A | 2/1990 | Williams | 604/264 |
| 4,936,834 A | 6/1990 | Beck et al. | 604/264 |
| 4,966,162 A | 10/1990 | Wang | 128/750 |
| 4,968,307 A | 11/1990 | Dake et al. | 604/264 |
| 5,125,910 A | 6/1992 | Freitas | 604/264 |
| 5,167,646 A | 12/1992 | Swafford | 604/39 |
| 5,190,519 A | 3/1993 | Mead et al. | 604/39 |
| 5,257,973 A | 11/1993 | Villasuso | 604/49 |
| 5,263,927 A | 11/1993 | Shlain | 604/13 |
| 5,295,952 A | 3/1994 | Pietrafitta | 604/15 |
| 5,304,187 A | 4/1994 | Green et al. | 604/13 X |
| 5,310,407 A | 5/1994 | Casale | 604/59 |
| 5,397,332 A * | 3/1995 | Kammerer et al. | 606/151 |
| 5,419,777 A | 5/1995 | Hofling | 604/264 |
| 5,503,623 A * | 4/1996 | Tilton, Jr. | 604/13 |
| 5,533,986 A | 7/1996 | Mottola et al. | 604/264 |
| 5,766,157 A * | 6/1998 | Tilton, Jr. | 604/264 |
| 5,797,899 A * | 8/1998 | Tilton, Jr. | 606/1 |
| 5,919,184 A * | 7/1999 | Tilton, Jr. | 606/1 |
| 6,010,495 A * | 1/2000 | Tilton, Jr. | 606/1 |

* cited by examiner

Primary Examiner—Kevin Shaver
Assistant Examiner—Brian Szmal
(74) Attorney, Agent, or Firm—Garvey, Smith, Nehrbass & Doody, LLC; Charles C. Garvey, Jr.

(57) ABSTRACT

An endoscopic instrument includes an inner elongated instrument member that fits the bore of an outer elongated instrument member. The inner instrument member carries a flag that can be furled about the distal end portion of the inner instrument member. A sheet of surgical material to be dispensed into a patient's body cavity can be attached to the flag. The outer instrument member includes an articulating end portion that can be moved to deflect the end portion of the inner instrument member such as when the flag is unfurled inside a patient's body cavity.

25 Claims, 5 Drawing Sheets

INSTRUMENTATION FOR ENDOSCOPIC SURGICAL INSERTION AND APPLICATION OF LIQUID, GEL AND LIKE MATERIAL

CROSS-REFERENCE TO RELATED APPLICATIONS

This is a continuation-in-part of U.S. Ser. No. 09/021,564, filed Feb. 10, 1998, (now U.S. Pat. No. 6,010,495), which is a continuation-in part of U.S. Ser. No. 08/718,861, filed Sep. 24, 1996 (now U.S. Pat. No. 5,797,899, issued Aug. 25, 1998), which is a continuation-in-part of U.S. patent application Ser. No. 08/644,504, filed May 10, 1996, (now U.S. Pat. No. 5,766,157, issued Jun. 16, 1998), which is a continuation-in-part of U.S. patent application Ser. No. 08/625,098, filed Apr. 1, 1996, now U.S. Pat. No. 5,919,184, which is a continuation-in-part of U.S. patent application Ser. No. 08/407,409, filed Mar. 17, 1995 (now U.S. Pat. No. 5,503,623, issued Apr. 2, 1996), all of which are incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a method and apparatus for endoscopic surgical (endo-surgical) introduction and application of surgical sheet material.

2. General Background of the Invention

Surgery performed within a body cavity (e.g., chest cavity, abdominal cavity) by means of endoscopic surgery utilizes of one or more surgical entry "ports" in varying size. The majority of sizes is in the range of five (5) millimeters to fifteen (15) millimeters, but may be as small as approximately two (2) millimeters. Each port consists of a tube with proximal and distal ends. A valve structure on the proximal end of the port member allows instruments to be passed through the body cavity wall while maintaining appropriate intra-cavity $CO_2$ (or other gas) pressure (if such pressure is required).

While instruments pass easily through the associated port member and its valve structure, sheet like material, liquids, gels, and like medicinal materials cannot be easily administered in endoscopic surgery.

In endoscopic surgery, there are or will be a variety of sheet material, liquid, gel and like medicinal materials that require application in the body cavity (including the pelvis). Because these products have specific medical purposes (example: adhesion prevention and as a drug delivery vehicle) the application will have to be precise (to targeted areas or tissues) as opposed to the general way irrigating solutions are administered to wash or rinse tissues during surgery. Also, because these products will be expensive they cannot be wasted and precise application is desired.

A number of patents have issued for surgical instruments some of which contemplate endoscopic deployment. For example, U.S. Pat. No. 5,304,187 issued to David Green et al., and entitled "Surgical Element Deployment Apparatus", provides an apparatus which facilitates endoscopic deployment and positioning of surgical elements adjacent to body tissue for subsequent securement thereto. The surgical element is wound within a tubular sleeve and then extruded from the distal end of the tubular sleeve. A method is also disclosed for deploying and positioning surgical elements using the apparatus of the present invention.

The Pietrafitta U.S. Pat. No. 5,295,952, entitled "Swab For Laparoscopy" discloses a swab that comprises an outer generally tubular shank with a handle or gripping end and a working end. An inner shaft is slidably received in the shank and has a working end and a gripping end. A changeable, disposable absorbent tip is operably connected to the working end of the shaft. The swab includes a biasing means at the gripping ends of the shank and shaft for urging the absorbent tip toward the gripping ends.

In the Shlain U.S. Pat. No. 5,263,927, entitled "Apparatus And Methods For Dispensing Surgical Packing", a surgical packing dispenser is disclosed that comprises an elongate tube having a housing mounted on its proximal end. A continuous roll of sterilized packing material is disposed within the housing, and a free end of the packing material extends distally through the tube. The sterilized packing material is mounted on the spindle, and a handle is provided to rotate the spindle to feed material from the roll down the dispenser tube. In this way, relatively lengthy amounts of the packing material can be dispensed during laparoscopic and other endoscopic surgical procedures.

In the Villasuso U.S. Pat. No. 5,257,973, entitled "Sealing Sleeve And Method For Laparoscopy", a sealing sleeve is disclosed for use with a cannula in open laparoscopy. The sleeve of the subject invention has a conical shaped collar defining a passageway for feeding the cannula there through. The collar is formed of a resilient medically inert material capable of conforming to the edges of an incision thereby forming a gas tight seal and maintaining the pneumoperitoneum during the laparoscopy. The sleeve also includes a polygonal tube connected to the collar and rigid supports attached to the polygonal tube for receiving a suture to maintain the cannula in place with respect to the patient.

The Casale U.S. Pat. No. 5,310,407, entitled "Laparoscopic Hemostat Delivery System And Method For Using Said System", discloses a delivery system and method for inserting hemostatic material through a channel of a laparoscopic cannula, and for directly applying the material to an internal tissue site, includes a hollow sheath having a cross-section and configuration that permits sliding passage thereof through the channel of the laparoscopic cannula. The sheath is charged with hemostatic material, and the hemostatic material is advanced through the lumen of the sheath and mechanically applied at the tissue site by an applicator. The hemostatic material may be in the form of compressed loose fibers, a sponge, a powder, a paste, a sheet, or a combination thereof, and may be composed of resorbable collagen.

BRIEF SUMMARY OF THE INVENTION

The present invention provides an improved instrument for endoscopic surgical insertion and application of surgical sheet material. The present invention also provides a method of placing surgical sheet material into a patient's body cavity such as, for example, the abdominal cavity, chest cavity, or the like.

The present invention provides an endoscopic surgical instrument that includes an outer elongated instrument body having an open ended bore and proximal and distal end portions. An inner elongated instrument body fits inside the bore of the outer instrument body, the inner instrument body having proximal and distal end portions, at least the distal end portion being flexible or articulated.

A flag member is mounted to the distal end of the inner instrument member, the flag member being sized and shaped to support a sheet of surgical material to be placed within the body cavity of a patient.

An optional articulating joint is provided at the distal end portion of the outer instrument body. The combination of the distal end of the inner instrument body and the flag furled about the distal end can be fitted within the bore of the outer instrument body of the distal end portion thereof. Means is provided for deploying the distal end of the inner instrument member beyond the distal end of the outer instrument member so that the flag can be opened to deploy the sheet of material inside the patient's body cavity.

The joint is preferably an articulating joint that can include a pivot.

The flag member is preferably a plastic material having a memory (or a preloaded cartridge) so that it automatically opens when the flag is discharged beyond the distal end of the outer instrument body into the patient's body cavity. This action opens the flag and presents the sheet of material to the proper location within the patient's body cavity.

The outer instrument body has a slot that receives the flag member so that the flag member can be furled about the inner instrument member and inside the bore of the outer instrument member by rotating the inner and outer instrument members in opposite relative rotational directions.

A clamp can be provided for holding an edge of the sheet of surgical material on the flag next to the inner instrument member.

The clamp is preferably a U-shaped member that fits the instrument member for gripping the edge of the surgical sheet material that the surgeon places on the flag.

A trigger mechanism is provided for pulling the clamp from the flag in order to release the sheet material from the flag once inside the patient's body cavity.

The inner instrument body can be provided with a plurality of openings, preferably linearly arranged. The openings can be subjected to suction for holding the material to be dispensed to the inner instrument member. The material to be dispensed can then be released by releasing the suction. The openings can also function as dispensing openings for dispensing a volume of liquid (such as normal saline). The liquid (e.g. saline) flows through the holes causing the sheet like material to "float" off, or detach from the flag member. This feature may be required when the sheet like material is stuck to the flag member by a small static or van der Waal type interaction present between the material and the flag. When using the linearly arranged openings, the U-shaped clamp or hood may not be required.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE INVENTION

Figure 1:
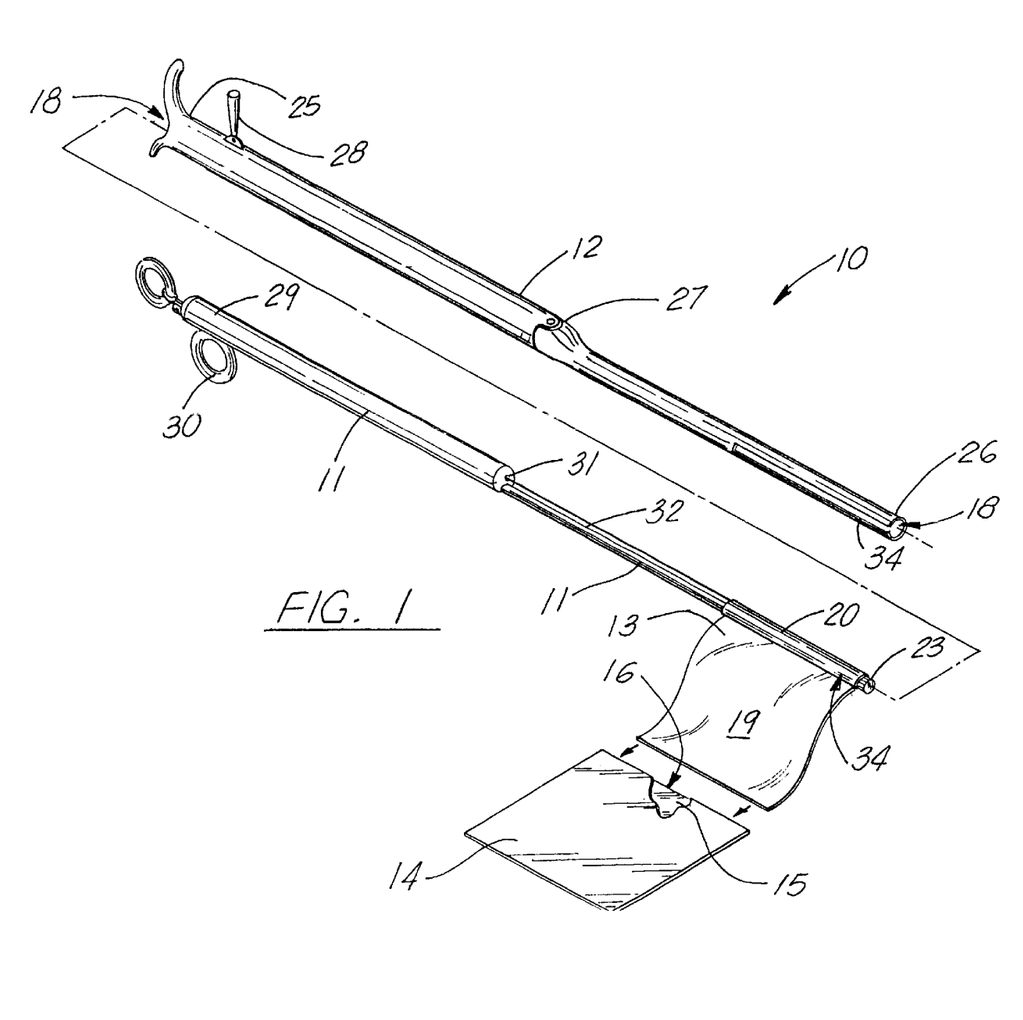
FIG. 1 is a perspective exploded view of the preferred embodiment of the apparatus of the present invention.
Figure 2:
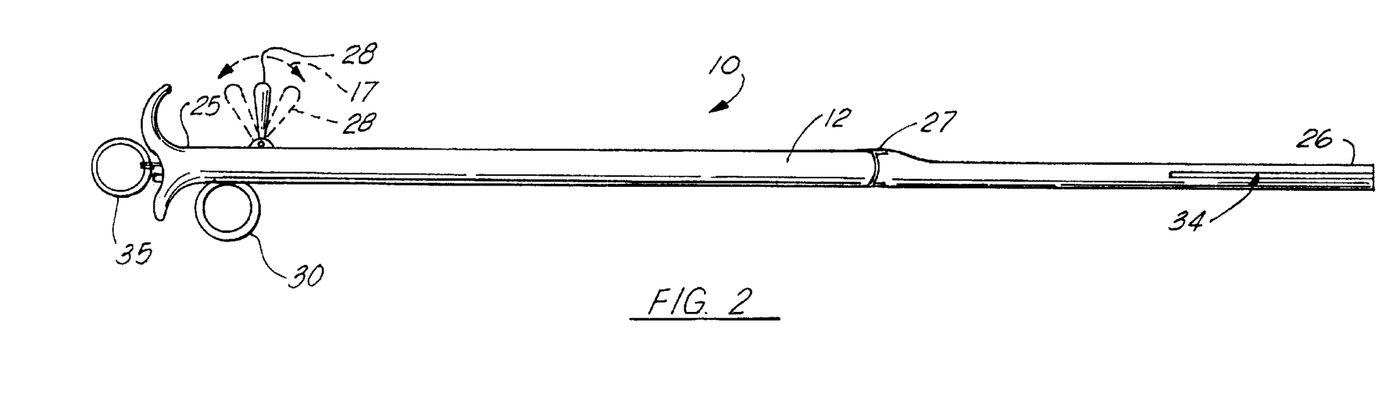
FIG. 2 is a side elevational view of the preferred embodiment of the apparatus of the present invention.
Figure 3:
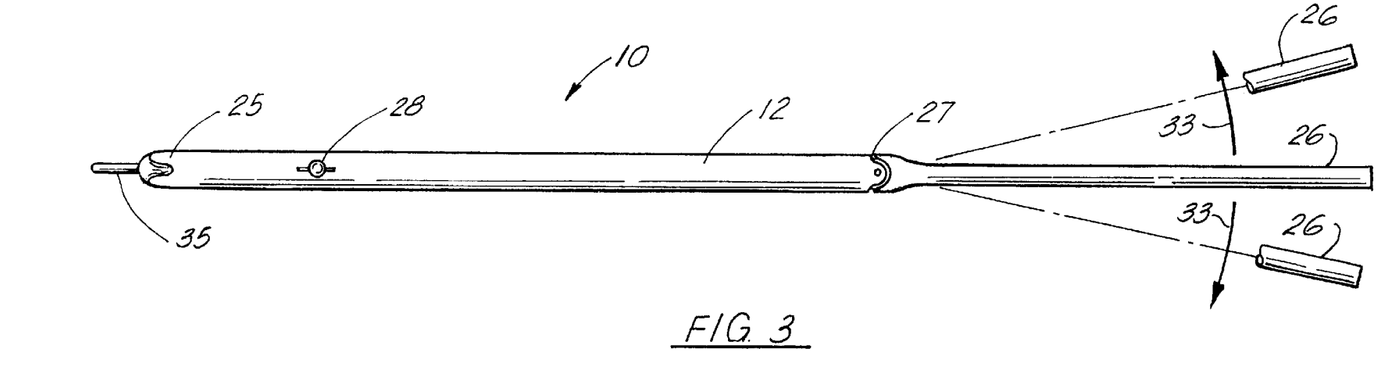
FIG. 3 is a top plan view of the preferred embodiment of the apparatus of the present invention.

FIGS. 1–7 show the preferred embodiment of the apparatus of the present invention designated generally by the numeral 10 in FIGS. 1–3. Endoscopic surgical instrument 10 includes an inner instrument member 11 and an outer instrument member 12, the inner member 11 preferably being flexible and the outer member 12 being articulated. The outer instrument 12 includes a proximal end portion 25 and a distal end portion 26.

Outer instrument member 12 provides a jointed portion that is preferably an articulating joint 27. Joint 27 can be operated with lever 28 to move in a pivotal fashion as shown by arrows 33 in FIG. 3. The use of lever 28 to operate distal end portion 26 of outer instrument body 12 is illustrated by arrow 17 in FIG. 2 and can be seen in prior U.S. Pat. Nos. 5,503,623, 5,766,157, and 5,797,899 and in co-pending prior patent application Ser. Nos. 08/625,098 and 09/021,564, all of which are hereby incorporated herein by reference.

In FIG. 1 of U.S. Pat. No. 5,503,623, the jaws open and close in parallel; opening and closing could be scissors-like in action, though opening and closing in parallel is preferred.

Inner instrument member 11 has proximal end 29 with handle 30 and distal end 23. A flag 13 of preferably rectangular shape is supported at the distal end portion 23 of inner instrument member 11 as shown in FIG. 1. The flag 13 is preferably attached to the inner instrument member 11 so that when the inner instrument member 11 is rotated, the flag 13 will furl about the distal end portion 23 of the inner instrument member 11. Flag 13 can be of a material such as polypropylene or polyethylene among others.

Envelope 14 is preferably a disposable envelope that contains a surgical sheet material 15 to be implanted in the patient. This surgical sheet material can be, for example Seprafilm® (Genzyme), Interceed® (Johnson & Johnson), Repel® (Life Medical), Incert® (Anika) or other hyaluronic acid or collagen derived materials. Some materials do not require an envelope, so envelope 14 is optional in some cases.

Figures 8, 9:
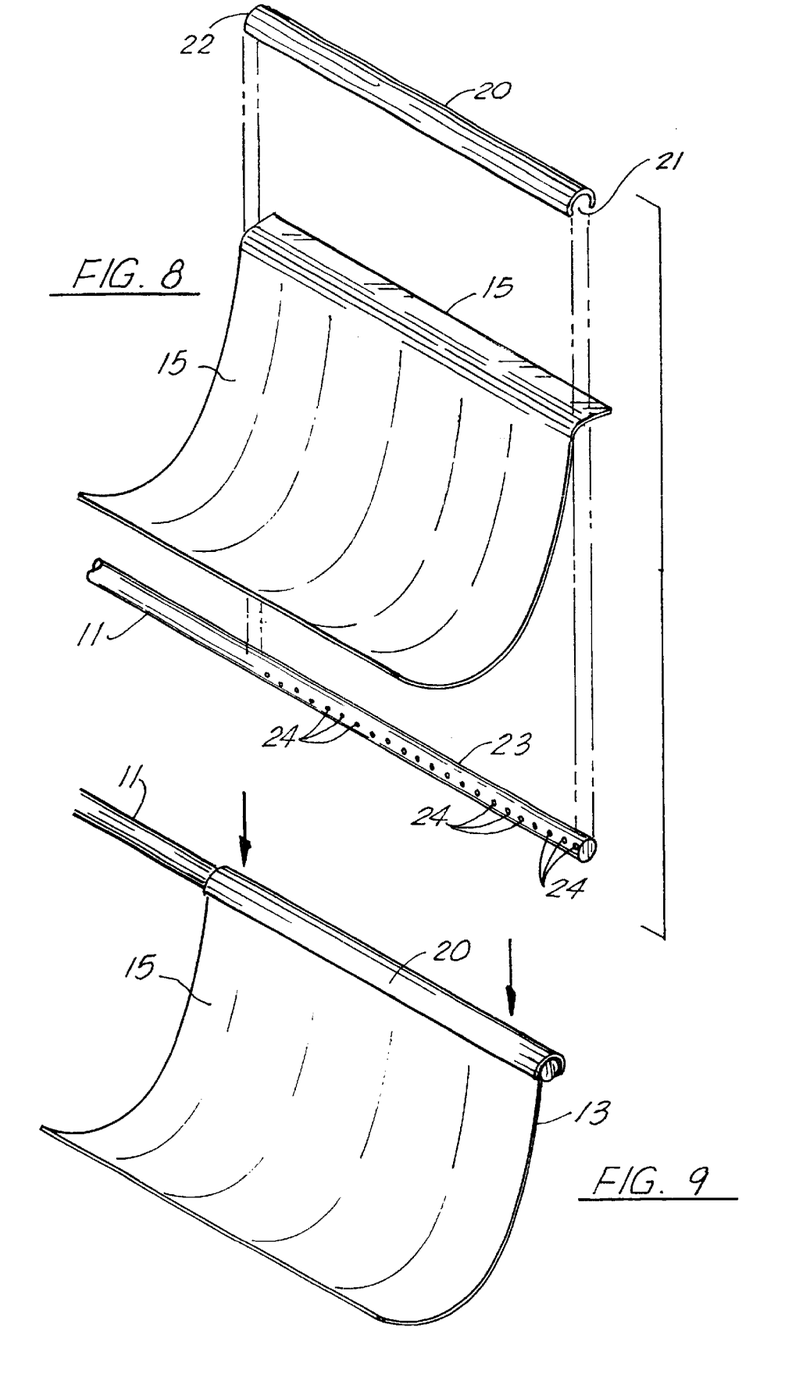
FIG. 8 is a partial perspective view of the preferred embodiment of the apparatus of the present invention illustrating connection of the surgical sheet material to the distal end portion of the inner instrument member.
FIG. 9 is a partial perspective view of the preferred embodiment of the apparatus of the present invention showing attachment of the surgical sheet material to the distal end portion of the inner instrument member.

Surgical sheet material 15 provides an edge 16 to be attached to flag member 13 that is supported by distal end portion 23 of inner instrument member 11. Alternatively, some surgical sheet material (for example Seprafilm®) will adhere to the plastic flag 13 without the need to attach edge 16 to inner instrument member In FIGS. 1, 5 and 8–9, a U-shaped clamp or hood 20 can be used to connect the edge 16 of surgical sheet material 15 to the distal end portion 23 of instrument member 11. In FIGS. 1 and 8–9, it can be seen that the edge 16 of sheet material 15 can be held to the distal end 23 of inner instrument member 11 with U-shaped hood 20. The U-shaped hood 20 provides a longitudinally extending recess 21 surrounded by a U-shaped or C-shaped wall 22.

Distal end 26 of outer instrument member 12 provides slot 34 through which flag member 13 extends when it is unfurled. The slot 34 also receives edge 16 so that the combination of sheet of material 15 and flag 13 can be furled (see arrow 37 in FIG. 4) about distal end portion 23 of inner instrument member 11 inside bore 18 of outer instrument member 12.

Furling (see FIG. 4) can be accomplished by holding the outer instrument member 12 while rotating the inner instrument member 11 so that the flag member 13 and the attached surgical sheet material 15 furl about the distal end portion 23 of inner instrument member 11. During furling of the flag member 13, surgical sheet material 15 rests upon surface 19 of flag 13 and is wrapped with the flag 13 about distal end portion 23 of inner instrument member 11.

During a surgical procedure, the surgeon places the assembly of inner instrument member 11 and flag member 13 with sheet 15 into the bore 18 of outer instrument member 12. The bore 18 can be open ended, extending the full length of outer instrument member 12 between its end portions 25, 26. Inner instrument member 11 fits within the bore 18 of outer instrument member 12 so that the overall assembly can be inserted through a standard endoscopy port (not shown) for surgery.

Flag member 13 carrying surgical sheet material 15 furled about inner instrument member 11 is positioned at the distal end 23 and within bore 43. The proximal end 29 of inner instrument member 11 provides a handle 30 that can aid in moving inner instrument member 11 into the bore 18 of outer instrument member 12. Handle 30 also enables inner instrument member 11 to be slided with respect to outer instrument member 12. An elongated slot on outer instrument body 12 proximal end 25 can receive handle 30. This enables handle 30 to extend distal end 23 of inner instrument member 11 beyond the distal end 26 of outer instrument member 12 such as during furling (see arrows 36, FIG. 4). The assembly of these two members 11, 12 is shown in FIGS. 1, 2 and 3.

The trigger end portion of the apparatus 10 can be any ergonomically designed arrangement that includes the control and positioning portions of the apparatus of the present invention. This would also include the trigger mechanism such as the pull ring 35.

Inner instrument member 11 has a bore 31 that carries cable 32. The cable 32 is used to deploy the flag member 13 and a surgical sheet material 15 mounted thereon, once the surgeon has placed the distal end portion 23 of the inner instrument member 11 through the endoscopy port and into the patient's body cavity for placement.

Figures 4, 5:
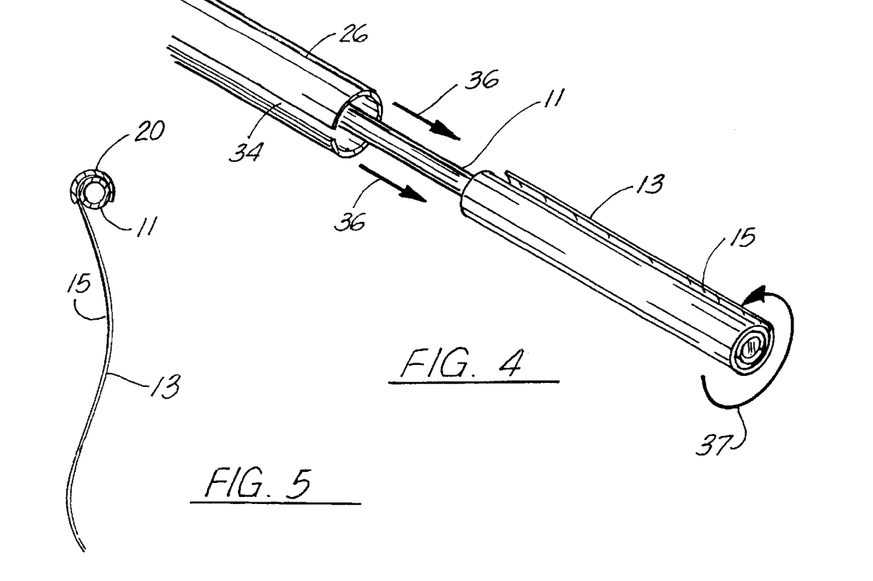
FIG. 4 is a perspective fragmentary view of the preferred embodiment of the apparatus of the present invention.
FIG. 5 is a partial sectional view of the preferred embodiment of the apparatus of the present invention.
Figure 6:
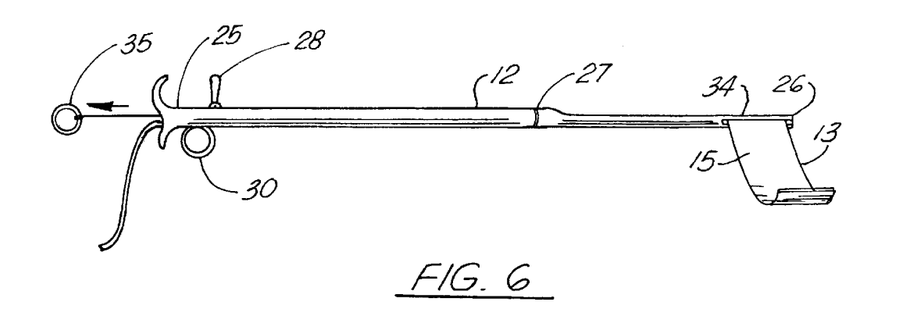
FIG. 6 is a perspective view of the preferred embodiment of the apparatus of the present invention showing the flag portion in an extended position.
Figure 7:
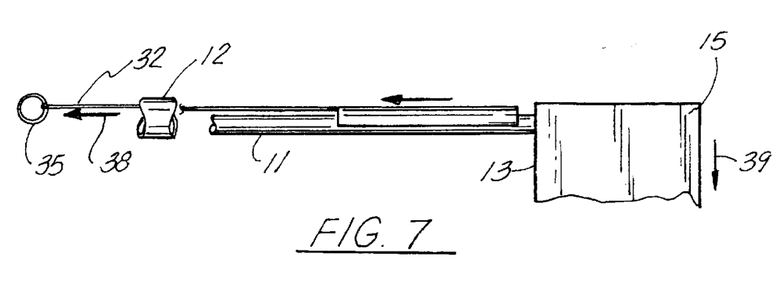
FIG. 7 is a fragmentary side view of the preferred embodiment of the apparatus of the present invention illustrating deployment of the flag portion.

In FIGS. 6–7, the flag member 13 can be opened to dispense surgical sheet material 15 by pulling ring 35 and its attached cable 32. Ring 35 and cable 32 are pulled in the direction of arrows 38 in FIGS. 6–7. Cable 32 pulls U-shaped hood 20 from flag 13 and sheet 15. The flag 13 can be of a plastic material that has a memory so that it opens once distal end portion 23 of inner instrument member 11 is extended beyond distal end 26 of outer instrument member 12, as indicated schematically by arrow 39 in FIG. 7. In FIG. 4, arrows 36 show the distal end of the inner instrument member 11 containing flag 13 and surgical sheet material 15. Flag 13 and surgical sheet material 15 unfurl due to the memory of the flag 13 which has the surgical sheet material 15 attached to it. This is also shown in FIGS. 5, 6 and 7. Arrow 39 in FIG. 7 schematically indicates the unfurling of surgical sheet material 15 from flag 13 when ring 32 is pulled in the direction of arrows 38 in order to remove U-shaped hood 20 from flag 13 and surgical sheet material 15. As shown in FIG. 7 of U. S. patent application Ser. No. 09/021,564 the nozzle can have an array of openings spaced along one side portion of the nozzle.

In FIGS. 8–9, distal end portion 23 of inner instrument member 11 can be provided with a plurality of openings 24. Fluid can be transmitted to openings 23 via a central bore of inner instrument body 11 for assisting in the removal of sheet 15 from flag 13 by flowing the fluid over surface 19 of flag 13, washing sheet 15 therefrom.

The openings 24 are preferably linearly arranged as shown in FIGS. 8 and 9. The linearly arranged holes 24 can be used either for holding the surgical sheet material 15 in place or for delivering a small volume of liquid (such as normal saline) through the holes 24. The dispensed liquid such as saline causes the sheet like material 15 to "float" off or detach it from the flag member 13. At times, the surgical sheet like material 15 can become stuck to the flag because of a small static or van der Waal type interaction present between the material 15 and flag 13. For this type of material, the U-shaped clamp 20 may not be necessarily required for the apparatus 10 to function properly.

Figures 10, 11, 12:
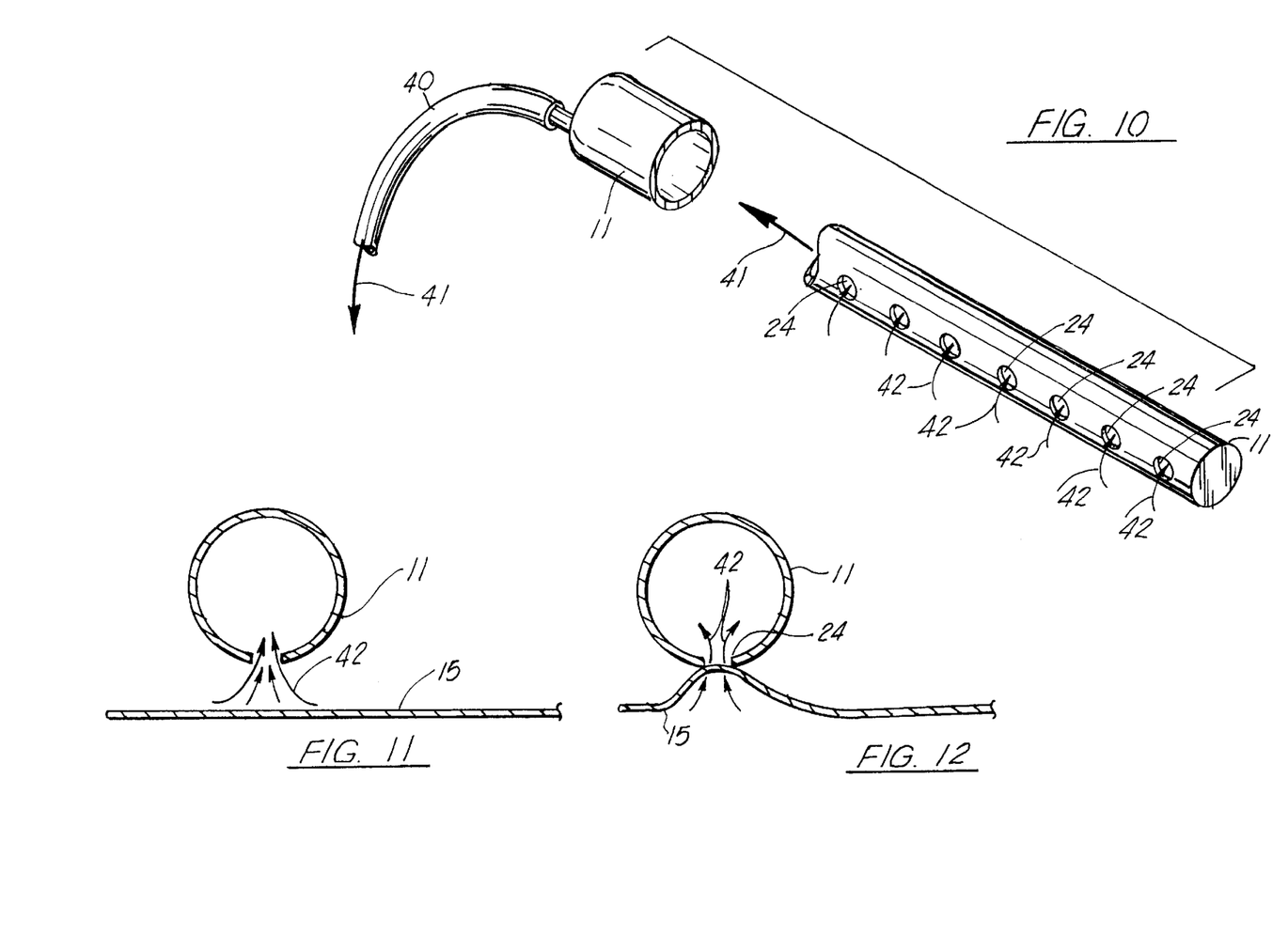
FIG. 10 is a partial perspective view of the preferred embodiment of the apparatus of the present invention showing the distal end portion of the inner instrument member and its use in moving the surgical sheet material during a surgical procedure.
FIG. 11 is a fragmentary view illustrating schematically the use of the distal end portion of the inner instrument member to move the surgical sheet material during surgery.
FIG. 12 is a fragmentary view illustrating schematically the use of the distal end portion of the inner instrument member to move the surgical sheet material during surgery.

In FIGS. 10–12, a suction via flowline 40 can be pulled in the direction of arrows 41, 42 so that openings 24 can be used to grip and manipulate sheet 15 once it is surgically placed inside of a patient's body cavity.

The following table lists the parts numbers and parts descriptions as used herein and in the drawings attached hereto.

PARTS LIST

| Part Number | Description |
|---|---|
| 10 | surgical instrument |
| 11 | inner instrument member |
| 12 | outer instrument member |
| 13 | flag member |
| 14 | envelope |
| 15 | surgical sheet material |
| 16 | edge |
| 17 | arrow |
| 18 | bore |
| 19 | surface |
| 20 | U-shaped hood |
| 21 | recess |
| 22 | wall |
| 23 | distal end |
| 24 | opening |
| 25 | proximal end |

-continued

PARTS LIST

| Part Number | Description |
|---|---|
| 26 | distal end |
| 27 | articulating joint |
| 28 | lever |
| 29 | proximal end |
| 30 | handle |
| 31 | bore |
| 32 | cable |
| 33 | arrow |
| 34 | slot |
| 35 | pull ring |
| 36 | arrow |
| 37 | arrow |
| 38 | arrow |
| 39 | arrow |
| 40 | conduit |
| 41 | arrow |
| 42 | arrow |

The foregoing embodiments are presented by way of example only; the scope of the present invention is to be limited only by the following claims.

What is claimed is:

1. An endoscopic surgical instrument comprising:
   a) an outer elongated instrument body having an open ended bore and proximal and distal end portions;
   b) an inner elongated instrument body that fits inside the bore of the outer instrument body, the inner instrument body having proximal and distal end portions, at least the distal end portion being flexible;
   c) a flag member mounted to the distal end of the inner instrument member, the flag member being sized and shaped to support a sheet of surgical material to be placed within the body cavity of a patient;
   d) an articulating joint at the distal end portion of the outer instrument body;
   e) wherein the combination of the distal end of the inner instrument body and the flag furled about the said distal end can be fitted within the bore of the outer instrument body at the distal end portion thereof; and
   f) means for deploying the distal end of the inner instrument member beyond the distal end of the outer instrument member so that the flag can be opened to deploy the sheet material inside the patients body cavity.

2. The surgical endoscopic instrument of claim 1 wherein the joint includes a pivot.

3. The surgical endoscopic instrument of claim 1 wherein the flag is plastic.

4. The surgical endoscopic instrument of claim 1 wherein the outer instrument body has a slot that receives the flag member so that the flag member can be furled about the inner instrument member and inside the bore of the outer instrument member by rotating the inner and outer instrument members in opposite rotational directions relative to one another.

5. The surgical endoscopic instrument of claim 1 further comprising a clamp for holding the edge of a sheet of surgical sheet material on the flag.

6. The surgical endoscopic instrument of claim 1 further comprising means for holding the sheet of surgical sheet material on the flag.

7. The surgical endoscopic instrument of claim 1 further comprising a clamp that fits the inner instrument member for gripping the edge of a sheet of surgical sheet material that is place by a surgeon on the flag.

8. The surgical endoscopic instrument of claim 1 further comprising a unshaped clamp that fits the outer surface of the inner instrument member for gripping the edge of a sheet of surgical sheet material that is place by a surgeon on the flag.

9. The surgical endoscopic instrument of claim 7 further comprising a trigger for pulling the clamp from the flag in order to release the sheet material from the flag.

10. An endoscopic surgical instrument comprising:
   a) an outer elongated instrument body having an open ended bore and proximal and distal end portions;
   b) an inner elongated instrument body that fits inside the bore of the outer instrument body, the inner instrument body having proximal and distal end portions, at least the distal end portion being flexible;
   c) a flag member mounted to the distal end of the inner instrument member, the flag member being sized and shaped to furl about the distal end of the inner instrument member and to support a sheet of surgical material to be placed within the body cavity of a patient;
   d) an articulating joint at the distal end portion of the outer instrument body, the distal end of the inner instrument member flexing distally of the articulating joint inside the distal end of the outer instrument member when the joint articulates;
   e) wherein the combination of the distal end of the inner instrument body and the flag furled about the said distal end can be fitted within the bore of the outer instrument body at the distal end portion thereof; and
   f) means for deploying the distal end of the inner instrument member beyond the distal end of the outer instrument member so that the flag can be opened to deploy the sheet material inside the patients body cavity.

11. An endoscopic surgical instrument comprising:
   a) an outer elongated instrument body having an open ended bore and proximal and distal end portions;
   b) an inner elongated instrument body that fits inside the bore of the outer instrument body, the inner instrument body having proximal and distal end portions, at least the distal end portion being flexible;
   c) a flag attached to the distal end of the inner instrument member;
   d) a surgical sheet-like material to be deployed, the sheet like material being furled during use about the distal end of the inner instrument member;
   e) dispensing openings on the distal end of the inner instrument member, the dispensing openings positioned to dispense fluid to the sheet like material and deploy it;
   f) an articulating joint at the distal end portion of the outer instrument body;
   g) wherein the combination of the distal end of the inner instrument body and the surgical sheet like material furled about the said distal end can be fitted within the bore of the outer instrument body at the distal end portion thereof; and
   h) means for deploying the distal end of the inner instrument member beyond the distal end of the outer instrument member so that the flag can be opened to deploy the sheet material inside the patients body cavity.

12. The surgical endoscopic instrument of claim 11 wherein the joint includes a pivot.

13. The surgical endoscopic instrument of claim 11 wherein the inner instrument member has a bore to which a vacuum can be attached for drawing a vacuum on the dispensing surgical sheet like openings so that material can be gripped.

14. The surgical endoscopic instrument of claim 11 wherein the member has a bore that can receive fluid to be transmitted to the dispensing openings.

15. The surgical endoscopic instrument of claim 11 further comprising a source of vacuum attachable to the proximal end portion of the inner instrument member.

16. The surgical endoscopic instrument of claim 1 further comprising a source of liquid that flows into the combination of inner and outer instrument bodies during said deployment.

17. The surgical endoscopic instrument of claim 7 further comprising a suction attachable to the combination of inner and outer instrument bodies for enabling a surgeon to manipulate the surgical sheet like material with the dispensing openings.

18. An endoscopic surgical instrument comprising:
   a) an outer elongated instrument body having an open ended bore and proximal and distal end portions;
   b) an inner elongated instrument body that fits inside the bore of the outer instrument body, the inner instrument body having proximal and distal end portions, at least the distal end portion being flexible;
   c) a sheet of surgical material to be placed within the body cavity of a patient, said sheet of material being removably attached to the inner instrument body;
   d) an articulating joint at the distal end portion of the outer instrument body, the distal end of the inner instrument member flexing distally of the articulating joint inside the distal end of the outer instrument member when the joint articulates;
   e) a source of fluid removably attachable to the inner instrument body for enabling a surgeon to manipulate and deploy the sheet of material inside a patients body cavity.

19. The surgical endoscopic instrument of claim 1 wherein the sheet of surgical material is in the form of a pre-loaded cartridge.

20. The surgical endoscopic instrument of claim 1 wherein the inner instrument member is flexible.

21. The surgical endoscopic instrument of claim 1 wherein the outer instrument member is flexible.

22. An endoscopic surgical instrument for inserting a surgical sheet article into a patient's body cavity comprising:
   a) an instrument body that includes a first member having a bore, a proximal end portion and a distal end portion;
   b) a second member that slides in the bore of the first member between first and second positions;
   c) a set of longitudinally extended jaws positioned at the distal end of the second member, said jaws being active jaws that are operable between open and closed positions, the jaws having respective gripping surfaces that are parallel to one another in the open and closed positions;
   d) a tubular cannula through which the instrument body can be inserted during a surgical endoscopic procedure so that the distal end of the instrument body, the jaws, and a gripped surgical sheet article can communicate with the patient's body cavity when the instrument body is inserted through the cannula;
   e) wherein the jaws abut along substantially their entire length enabling them to grip and support the surgical sheet article, and of a shape that enables the sheet article to be furled about the jaws inside the bore of the first member;
   f) the second member defining an operator with a handle that can be manipulated by a surgeon at its proximal end portion for enabling an opening and closing of the jaws;
   g) wherein the jaws have a cross section that fits inside the bore of the first member that enlarges when the jaws open beyond the distal end of the bore of the first member so that the sheet material can be released distally of the first member by opening the jaws; and
   h) wherein the second member is longer than the first member, enabling the jaws and furled sheet article to be discharged from and positioned beyond the distal end of the first member when the handle is manipulated by a surgeon to a position next to the proximal end of the first member so that the sheet can be unfurled and released from the jaws by manipulation of the handle to open the jaws after the jaws and furled sheet are positioned beyond the distal end of the first member and within the patient's body cavity without obstruction by the first member during the unfurling of the sheet.

23. A method of dispensing a selected liquid, gel or like medicinal material into the patient's body cavity, comprising the steps of:
   a) surgically forming a port through the patient's body cavity wall;
   b) the placement of said port including placing a first tubular member, having proximal and distal end portions and an elongated bore into the patient's body cavity;
   c) inserting a second tubular member into the bore of the first tubular member, the second tubular member being an instrument body with a distal end portion with a nozzle that can be rotated by the surgeon with respect to the first tubular member, the second tubular member having a central axis, an outer wall, and a row of dispensing openings positioned along a line generally parallel to the central axis and along one side portion of the nozzle;
   d) extending the distal end of the second tubular member and its nozzle into the patient's body cavity;
   e) rotating the nozzle to enable a surgeon to position the distal end in a desired rotational position for aiming a spray; and
   f) transmitting the liquid into the patient's body cavity via the nozzle.

24. The method of claim 23, wherein there are additional nozzle openings in one or more lines.

25. A method of inserting a surgical sheet article into a body cavity of a patient, comprising the steps of:
   a) surgically forming an opening in the patient's body wall;
   b) placing a tubular member, having proximal and distal end portions and an elongated bore, through the surgically formed opening;
   c) gripping the surgical sheet article with an inserter instrument having a pair of active jaws that can be opened and closed by the surgeon for enabling said gripping and releasing;
   d) furling the surgical sheet article into a roll about the active jaws of the inserter to define a furled sheet;
   e) placing the furled sheet into the bore of the tubular member so that the tubular member holds the surgical article sheet in a furled condition, wherein the sheet is furled about an axial line that coincides with a central longitudinal axis of the tubular member;

f) discharging the active jaws and surgical sheet article from the distal end portion of the tubular member and into the patient's body cavity;

g) placing the surgical sheet article against selected tissue; and h) releasing the sheet by opening the active jaws wherein the jaws have respective gripping surfaces that are parallel to one another in the open and closed positions.

* * * * *